US010820959B2

(12) United States Patent
Weber et al.

(10) Patent No.: US 10,820,959 B2
(45) Date of Patent: *Nov. 3, 2020

(54) MEDICAL DEVICE PACKAGING WITH POWER SOURCE

(71) Applicant: BOSTON SCIENTIFIC SCIMED, INC., Maple Grove, MN (US)

(72) Inventors: Jan Weber, Maastricht (NL); Daniel Burgess, St. Francis, MN (US); Kathryn A. Johnson, Maple Grove, MN (US); James M. Peck, Maple Grove, MN (US)

(73) Assignee: BOSTON SCIENTIFIC SCIMED, INC, Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/685,689

(22) Filed: Nov. 15, 2019

(65) Prior Publication Data

US 2020/0078126 A1 Mar. 12, 2020

Related U.S. Application Data

(63) Continuation of application No. 15/619,112, filed on Jun. 9, 2017, now Pat. No. 10,478,259.

(Continued)

(51) Int. Cl.
*H01M 10/46* (2006.01)
*A61B 50/30* (2016.01)
(Continued)

(52) U.S. Cl.
CPC ......... *A61B 50/30* (2016.02); *H01M 10/0436* (2013.01); *H01M 10/44* (2013.01);
(Continued)

(58) Field of Classification Search
CPC .......... H02J 7/0042; H02J 7/025; H02J 5/005; H02J 7/355; H02J 7/0021; H02J 50/10
(Continued)

(56) References Cited

U.S. PATENT DOCUMENTS 4,641,076 A 2/1987 Linden
6,782,290 B2 8/2004 Schmidt
(Continued)

FOREIGN PATENT DOCUMENTS

| JP | 2000287987 A | 10/2000 |
|---|---|---|
| WO | 2012037171 A2 | 3/2012 |
| WO | 2012037171 A3 | 3/2012 |

OTHER PUBLICATIONS

International Search Report and Written Opinion dated Sep. 19, 2017 for International Application No. PCT/US2017/036840.

*Primary Examiner* — Edward Tso
(74) *Attorney, Agent, or Firm* — Seager, Tufte & Wickhem, LLP

(57) ABSTRACT

A system for charging an onboard battery of a medical device prior to use of the medical device may include a package configured to accommodate the medical device therein. A power source may be disposed relative to the package and may be capable of charging the onboard battery of the medical device prior to use of the medical device. The system may be capable of being subjected to a sterilization process with the power source disposed within the second cavity. In some instances, the power source is uncharged during sterilization. In some cases, the power source is encapsulated or otherwise sealed during sterilization.

20 Claims, 11 Drawing Sheets

Related U.S. Application Data

(60) Provisional application No. 62/347,896, filed on Jun. 9, 2016.

(51) Int. Cl.
| | |
|---|---|
| *H01M 10/04* | (2006.01) |
| *H01M 10/44* | (2006.01) |
| *H02J 7/00* | (2006.01) |
| *H02J 7/02* | (2016.01) |
| *A61L 2/14* | (2006.01) |
| *A61B 90/00* | (2016.01) |

(52) U.S. Cl.
CPC ............ *H02J 7/0042* (2013.01); *H02J 7/025* (2013.01); *A61B 2050/3008* (2016.02); *A61B 2090/0813* (2016.02); *A61L 2/14* (2013.01)

(58) Field of Classification Search
USPC ........ 320/103, 107, 108, 114, 115, 132, 149
See application file for complete search history.

(56) References Cited

U.S. PATENT DOCUMENTS

| | | | |
|---|---|---|---|
| 9,000,720 B2 | 4/2015 | Stulen et al. | |
| 9,076,589 B2 | 7/2015 | Wright et al. | |
| 9,276,292 B1 | 3/2016 | MacKenzie et al. | |
| 2007/0048176 A1* | 3/2007 | Orrico | A61L 2/14 422/29 |
| 2008/0154178 A1 | 6/2008 | Carter et al. | |
| 2012/0116380 A1 | 5/2012 | Madan et al. | |
| 2012/0165620 A1* | 6/2012 | Tanis | A61B 5/1172 600/301 |
| 2013/0009606 A1 | 1/2013 | Smith et al. | |
| 2016/0187153 A1* | 6/2016 | Johnson | G16H 40/63 701/500 |
| 2017/0319108 A1* | 11/2017 | Donohoo | H04M 1/72572 |
| 2017/0331318 A1 | 11/2017 | Jankins et al. | |

* cited by examiner

MEDICAL DEVICE PACKAGING WITH POWER SOURCE

CROSS-REFERENCE TO RELATED APPLICATIONS

This application is a continuation of U.S. application Ser. No. 15/619,112 filed Jun. 9, 2017, now U.S. Pat. No. 10,478,259; which claims priority under 35 U.S.C. § 119(e) to U.S. Provisional Application No. 62/347,896, filed Jun. 9, 2016, the entire disclosures of which are herein incorporated by reference.

TECHNICAL FIELD

The disclosure is directed to medical devices that employ an onboard rechargeable battery as well as packaging for the medical devices that include a power source for charging the onboard rechargeable battery. More particularly, the disclosure is directed to such packaging that can safely be sterilized.

BACKGROUND

A number of medical devices include sensors, microprocessors, and other elements that require electrical power to function. While medical devices may include onboard batteries to supply electrical power, it will be appreciated that batteries sometimes tend to lose power during storage. Of the known medical devices and methods, each has certain advantages and disadvantages. There is an ongoing need to provide alternative medical devices as well as alternative methods for manufacturing and using medical devices.

SUMMARY

The disclosure is directed to several alternative designs, materials and methods of manufacturing medical device structures and assemblies, and uses thereof. For example, the disclosure is directed to systems for charging an onboard battery of a medical device prior to use of the medical device.

In an example of the disclosure, a system for charging an onboard battery of a medical device prior to use of the medical device is disclosed. The system includes a package defining a first cavity and a second cavity spaced apart from the first cavity. A medical device may be disposed within the first cavity of the package, the medical device including an onboard rechargeable battery disposed within the medical device. A power source may be disposed within the second cavity of the package and may be capable of charging the onboard battery of the medical device prior to use of the medical device. The system may be capable of being subjected to a sterilization process with the power source disposed within the second cavity.

Alternatively or additionally to any of the embodiments above, the power source includes a rechargeable battery.

Alternatively or additionally to any of the embodiments above, the rechargeable battery is uncharged during the sterilization process and is configured to subsequently be charged after the sterilization process.

Alternatively or additionally to any of the embodiments above, the rechargeable battery is at least partially encapsulated during the sterilization process.

Alternatively or additionally to any of the embodiments above, the rechargeable battery includes a printed battery that is separately printed and subsequently disposed within the second internal cavity.

Alternatively or additionally to any of the embodiments above, the rechargeable battery includes a printed battery that is printed onto a surface of the second cavity.

Alternatively or additionally to any of the embodiments above, the first cavity is internal to the package and/or the second cavity is internal to the package.

Alternatively or additionally to any of the embodiments above, the system further includes an inductive charger operably coupled to the power source for inductively charging the onboard battery of the medical device prior to use thereof.

Alternatively or additionally to any of the embodiments above, the system further includes a pair of electrical contacts operably coupled to the power source for directly charging the onboard battery of the medical device prior to use thereof.

Alternatively or additionally to any of the embodiments above, the system further includes a charging controller that is configured to be instructable to cause the power source to charge the onboard battery of the medical device prior to use thereof.

In another example of the disclosure, a system for charging an onboard battery of a medical device prior to use of the medical device is disclosed. The system includes a package configured to accommodate a medical device within an interior of the package as well as a medical device disposed within the interior of the package, the medical device including an onboard rechargeable battery disposed within the medical device. A printed battery may be capable of charging the onboard battery of the medical device prior to use of the medical device. The system may be capable of being subjected to a sterilization process with the printed battery disposed relative to a surface of the package.

Alternatively or additionally to any of the embodiments above, the package includes an internal surface, and the printed battery is disposed adjacent to the internal surface.

Alternatively or additionally to any of the embodiments above, the package includes an external surface, and the printed battery is disposed adjacent to the external surface.

Alternatively or additionally to any of the embodiments above, the printed battery includes a (+) terminal and a (−) terminal, and at least one of the (+) terminal and the (−) terminal includes an encapsulating layer sealing the terminal from atmosphere during the sterilization process.

Alternatively or additionally to any of the embodiments above, the encapsulating layer is configured to be removable prior to using the printed battery to charge the onboard battery of the medical device.

Alternatively or additionally to any of the embodiments above, the printed battery is printed in an initially uncharged state.

Alternatively or additionally to any of the embodiments above, the onboard battery of the medical device is sealed against the sterilization process.

In another example of the disclosure, a method of charging an onboard battery of a medical device using a package battery disposed within a package holding the medical device is disclosed. A printed battery that is configured to be safe during an ethylene oxide sterilization process may be disposed relative to the package. The package may be subjected to an ethylene oxide sterilization process. The printed battery may be charged so that the printed battery can be used to charge the onboard battery of the medical device.

Alternatively or additionally to any of the embodiments above, the method further includes using the printed battery to charge the onboard battery of the medical device.

Alternatively or additionally to any of the embodiments above, disposing a printed batter relative to the package includes printing a printed battery on a surface of the package.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
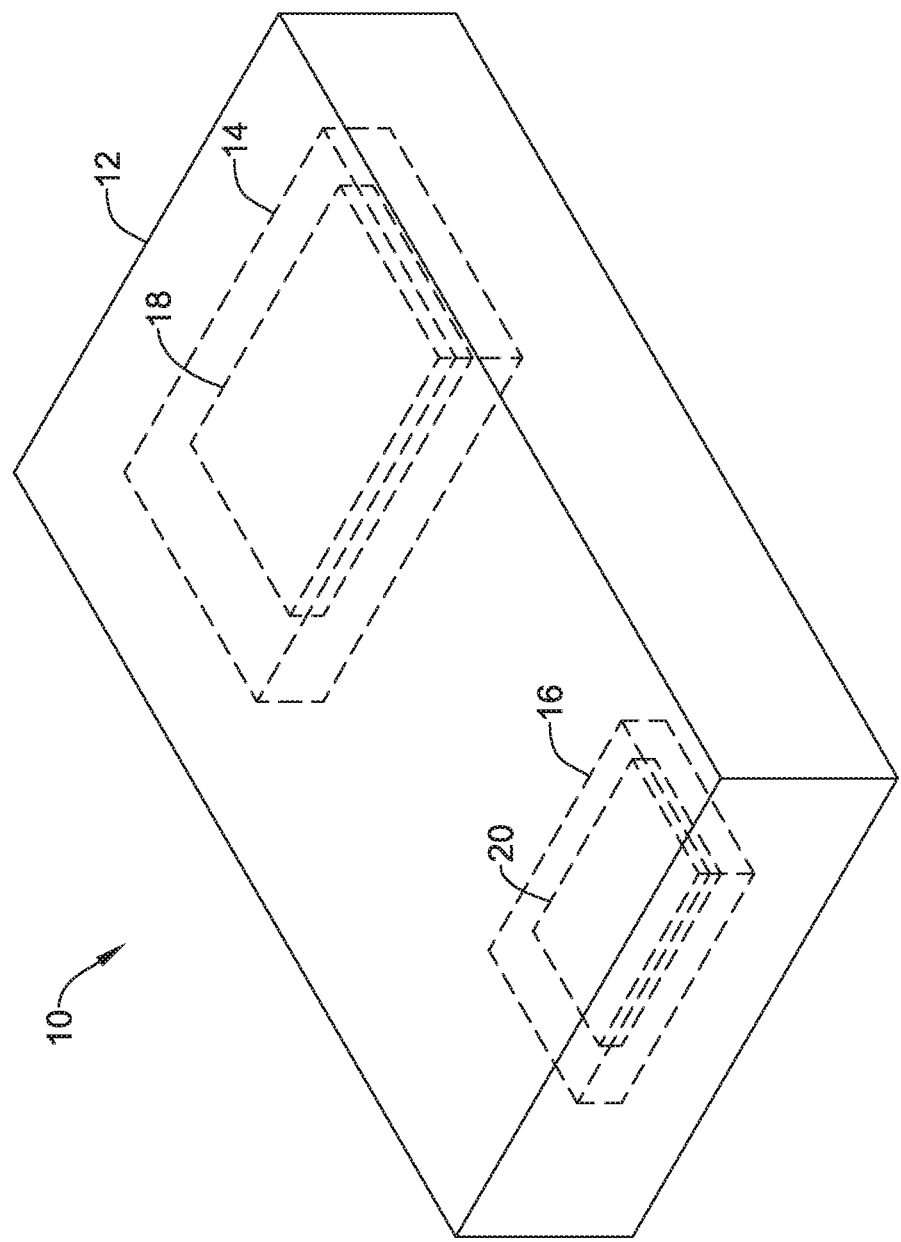
FIG. 1 is a schematic illustration of a system for charging an onboard battery of a medical device prior to use in accordance with an embodiment of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 provides a schematic illustration of a system 10 that may be used to charge an onboard battery of a medical device prior to use of the medical device. By charging the onboard battery of the medical device before use, such as immediately before use, the onboard battery will be fully charged. In contrast, if the onboard battery is previously charged, such as during or after assembly of the medical device, the onboard battery will lose power during storage. The system 10 includes a package 12. While the package 12 is illustrated as being rectilinear in shape, it will be appreciated that this is merely illustrative, as the package 12 may take any particular or desired shape in order to accommodate the size and shape of the medical device to be packaged within the package 12, for example.

In some instances, the package 12 may be considered as defining a first cavity 14 and a second cavity 16 that is spaced apart from the first cavity 14. A medical device 18 may be disposed within the first cavity 14. A power source 20 may be disposed within the second cavity 16. While a single first cavity 14 is shown, with a single medical device 18 disposed therein, it will be appreciated that in some cases the package 12 may be configured to accommodate multiple medical devices 18. In some cases, a single medical device 18 may be in multiple pieces or sections that can be assembled just prior to use. In some cases, a single medical device 18 may be provided in kit form, where particular elements or components, such as of differing size or function, may be provided within the package 12. In any of these cases, it will be appreciated that the first cavity 14 may include one or more distinct cavities formed within the package 12. In some cases, as will be discussed, the system 10 may be safely sterilized with the power source 20 disposed within the package 12.

In some cases, for example, the system 10 may be subjected to a radiative sterilization process such as e beam radiation or gamma radiation. In some cases, the system 10 may be subjected to sterilization via an ethylene oxide atmosphere. While ethylene oxide sterilization does not raise any potentially explosive concerns when operating properly, presumably well above the upper explosive limit, there can be concerns if the ethylene oxide sterilization process is not running correctly. For example, if the ethylene oxide concentration within the sterilizing atmosphere dropped below the upper explosive limit (but still above a lower explosive limit), there could be problems if a source of electricity is present. The disclosure describes ways of safely sterilizing a system that may include a power source.

Figure 2:
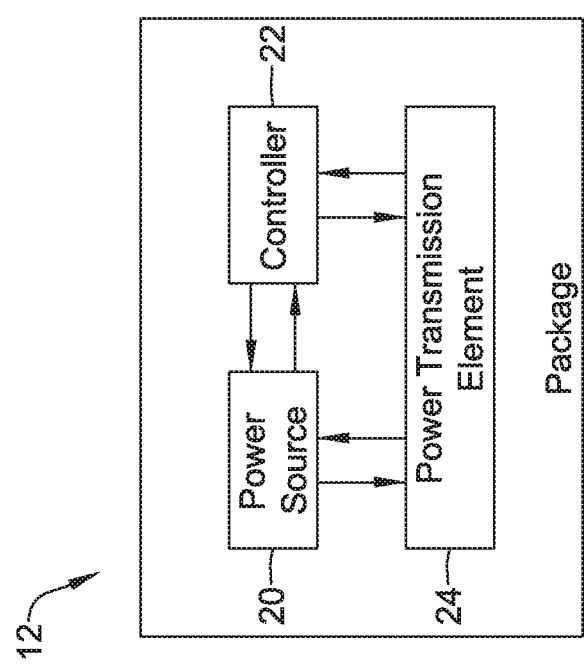
FIG. 2 is a schematic illustration of a package forming part of the system of FIG. 1.

FIG. 2 is a schematic illustration of the package 12, showing the power source 20. In some cases, the package 12 may include a controller 22 and a power transmission element 24. The controller 22 may, for example, be configured to regulate operation of the power transmission element 24 in charging the power source 20. In some cases, the controller 22 may also be configured to regulate operation of the power transmission element 24 in subsequently using electrical energy from the power source 20 to charge the onboard battery of the medical device 18 (FIG. 1). The power transmission element 24 may represent any suitable technique for transmitting power to and from the power source 20. In some cases, the power transmission element 24 may include an antenna for receiving RF energy, for example, and the controller 22 may include a rectifier circuit or functionality to convert the received RF energy into a form that may be used for charging the power source 20. An antenna within the power transmission element 24 may subsequently be used to transmit energy to the onboard battery of the medical device 18.

In some cases, the power source 20 may be a rechargeable battery that can be charged or recharged after sterilization. In some cases, the power source 20 may be a capacitor that can be charged after sterilization. In some cases, the power source 20 may include energy harvesting capability that can capture energy present in the environment, such as but not limited to chemical energy, thermal energy, radiant energy and mechanical energy. In some cases, the power source 20 may be configured to capture mechanical energy such as the vibrations that occur during shipping. In electrostatic energy harvesting, two plates are electrically isolated from each other via air, vacuum, or insulator. Movement of one plate relative to the other plate changes capacitance and thus increases total potential energy. A magnet moving relative to a coil can generate electricity. In some instances, the package 12 may include piezoelectric materials that can generate electricity in response to an applied mechanical strain. Any of these energy harvesting techniques may be used to at least partially charge the power source 20, or may be used to augment the power source 20. In some cases, one or more of these energy harvesting techniques may supplant the power source 20.

In some instances, the power source 20 may be a printed battery. In some cases, the power source 20 may be a zinc-based printed battery such as those available commercially from Imprint Energy of Alameda, Calif. It will be appreciated that as a printed battery, the power source 20 may be made to be any size that can fit into an interior of the package 12, such as the second cavity 16 shown in FIG. 1. In some cases, as will be discussed herein with respect to FIG. 4 and FIG. 5, the power source 20 may be disposed on any interior or exterior surface of the package 12. In some cases, a printed battery may be printed onto a suitable substrate and then disposed in or on the package 12. In some cases, a printed battery may be printed directly onto a surface of the package 12.

In some cases, a printed battery may be printed using appropriate chemical species to render the power source 20 initially uncharged. In some cases, the printed battery may be printed with chemical species that renders the power source 20 with an initial charge that may represent a full charge or a partial charge. In some cases, as will be discussed with respect to subsequent FIGS., the power source 20 may be at least partially encapsulated to seal the power source 20 during a sterilization process. Additional details regarding a suitable printed battery may be found in U.S. Pat. Nos. 9,076,589 and 9,276,292, both of which are incorporated by reference herein, in their entirety.

Figure 3:
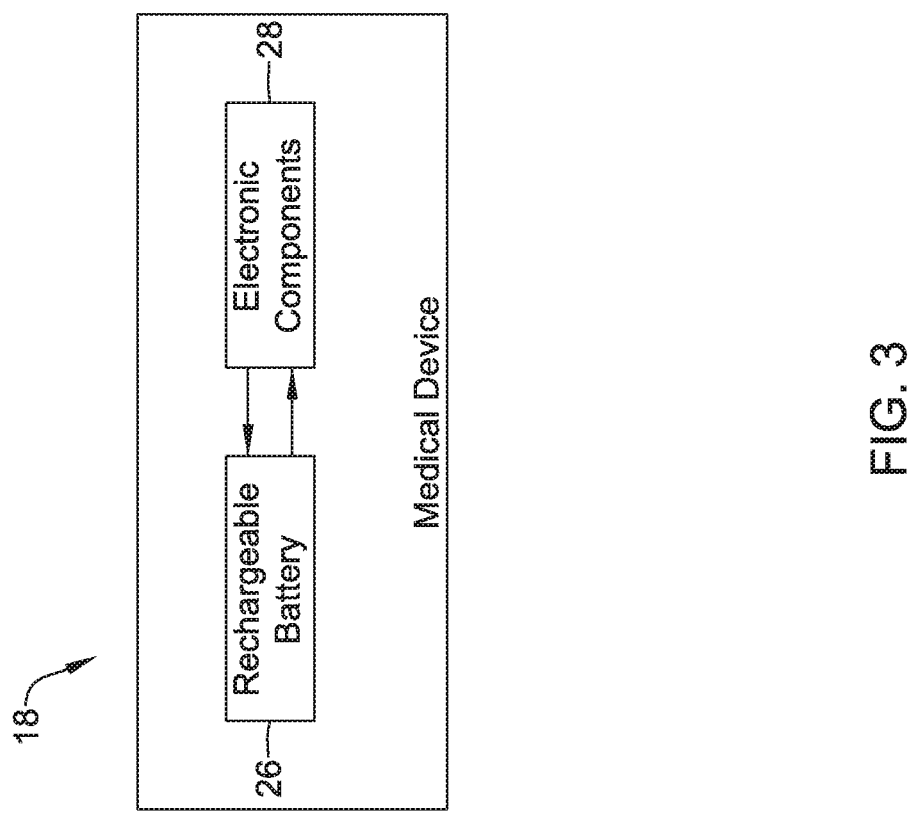
FIG. 3 is a schematic illustration of a medical device forming part of the system of FIG. 1.

FIG. 3 is a schematic illustration of the medical device 18. The medical device 18 may generally represent any variety of medical devices that consume electrical energy in the operation of the medical device 18. The medical device 18 includes a rechargeable battery 26, representing an embodiment of the aforementioned onboard battery, and electronic components 28. The electronic components 28 represent the power consuming portion of the medical device 18, and may include such things as sensors, actuators, communication elements, and the like. In some cases, the electronic components 28 may include an antenna or other communication elements that enable the medical device 18 to communicate with the package 12, such as with the controller 22 within the package 12.

In some cases, for example, this may permit the controller 22 to monitor a current charge within the rechargeable battery 26, and to provide a trickle charge to the rechargeable battery 26 while the medical device 18 remains within the package 12. In some cases, while not illustrated, the package 12 may include a display (not illustrated) upon which the controller 22 can provide a visual indication of a remaining charge level within the rechargeable battery 26. The controller 22 may instead display an indication of how soon the rechargeable battery 26 should be recharged, or how long the rechargeable battery 26 may be able to power operation of the medical device 18 given the current power levels within the rechargeable battery 26, for example. In such cases, there may be wireless communication between the medical device 18 and the package 12. In some cases, the package 12 may include wiring traces (not illustrated) that enable communication and/or power transfer between the medical device 18 and the package 12.

In some cases, the controller 22 may be configured to be aware of its current location. For example, the controller 22 may include a GPS capability, or be in communication with another device having GPS capability. Accordingly, the controller 22 may be configured to charge or recharge the rechargeable battery 26 only when the package 12 (and the medical device 18) are in a location where use may be imminent. In some cases, the controller 22 may only charge or recharge the rechargeable battery 26 when its current location indicates that the medical device 18 is near or within a hospital, for example.

In some cases, the controller 22 may include an internal clock, and may utilize its internal clock to periodically check a power level within the rechargeable battery 26. In some cases, for example, the controller 22 may check a power level within the rechargeable battery 26 on a regular interval, such as but not limited to once a month. It will be appreciated that this particular interval is merely illustrative, and any desired interval could be utilized. If the power level within the rechargeable battery 26 has dropped below a particular threshold, the controller 22 may proceed with recharging the rechargeable battery 26. Alternatively, if the power level is too low, or the controller 22 is unable to determine the power level, the package 12 may be flagged as defective, and removed from inventory and possibly returned to the manufacturer.

Figure 4:
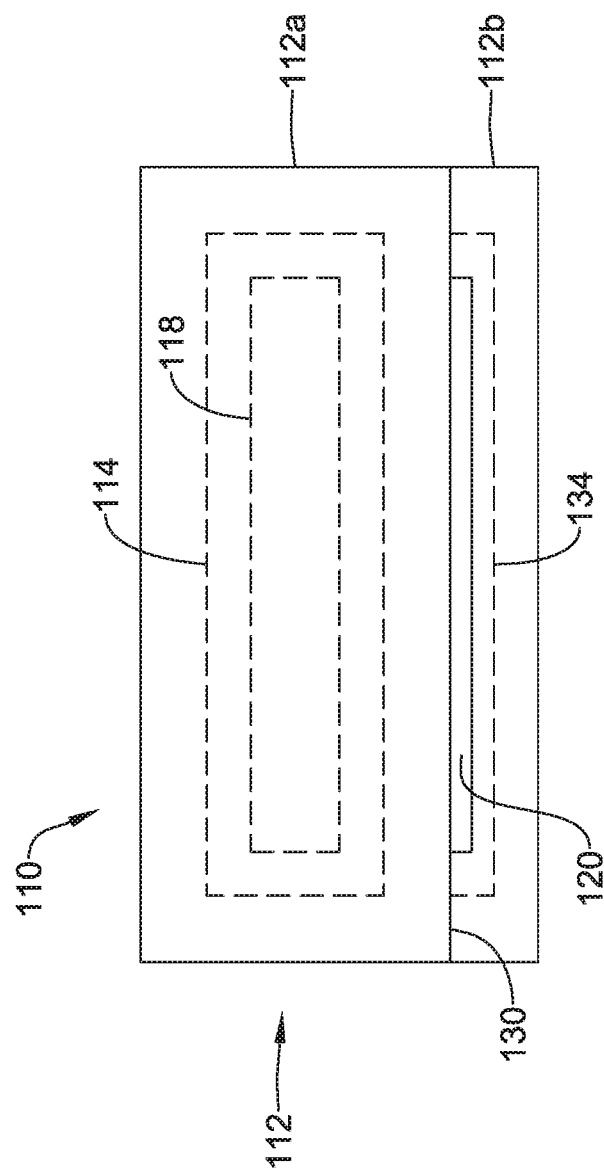
FIG. 4 is a schematic illustration of a system for charging an onboard battery of a medical device prior to use in accordance with an embodiment of the disclosure.
Figure 5:
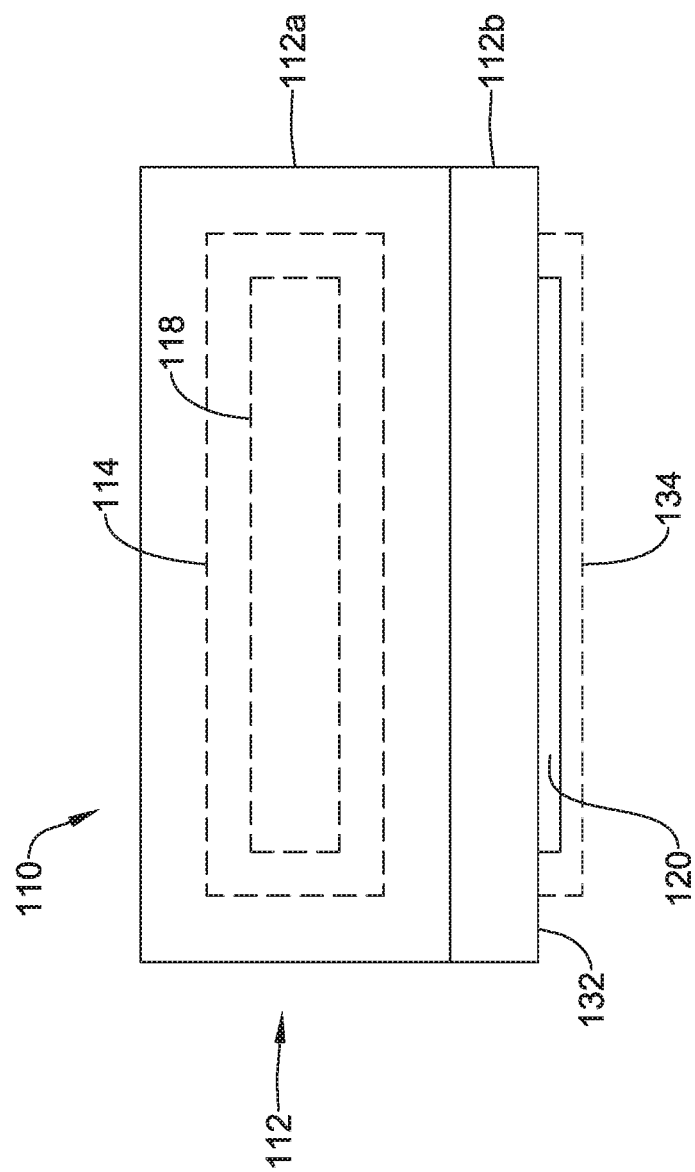
FIG. 5 is a schematic illustration of a system for charging an onboard battery of a medical device prior to use in accordance with an embodiment of the disclosure.

FIG. 4 and FIG. 5 are schematic illustrations of a system 110 including a package 112. In some cases, for example, the package 112 may include a first portion 112a and a second portion 112b. The first portion 112a and the second portion 112b may, for example, represent two portions of a clamshell-type package. In some cases, the package 112 may include additional layers or components. The package 112 defines an interior volume 114 that is sized and configured to accommodate a medical device 118. In some cases, the medical device 118 may be considered as representing the medical device 18, and may be any medical device that includes, as shown for example in FIG. 3, an onboard battery such as the rechargeable battery 26. The system 110 includes a power source 120 which may, for example, be considered as representing the power source 20 shown in FIG. 1 and FIG. 2.

In some cases, the power source 120 may be a printed battery. As shown in FIG. 4, the power source 120 may be adjacent to an internal surface 130 of the package 112. The power source 120, particularly if a printed battery, may be printed directly onto the internal surface 130 before the first portion 112a and the second portion 112b are assembled together. In some cases, the power source 120 may include a substrate upon which the printed battery is printed, and then is secured relative to the internal surface 130. In some cases, as shown in FIG. 5, the power source 120 may be adjacent to an external surface 132 of the package 112. The power source 120, particularly if a printed battery, may be printed directly onto the external surface 132. In some cases, the power source 120 may include a substrate upon which the printed battery is printed, and then is secured relative to the external surface 132. In some cases, the power source 120 may be encapsulated via an encapsulating layer or film 134.

Figure 6:
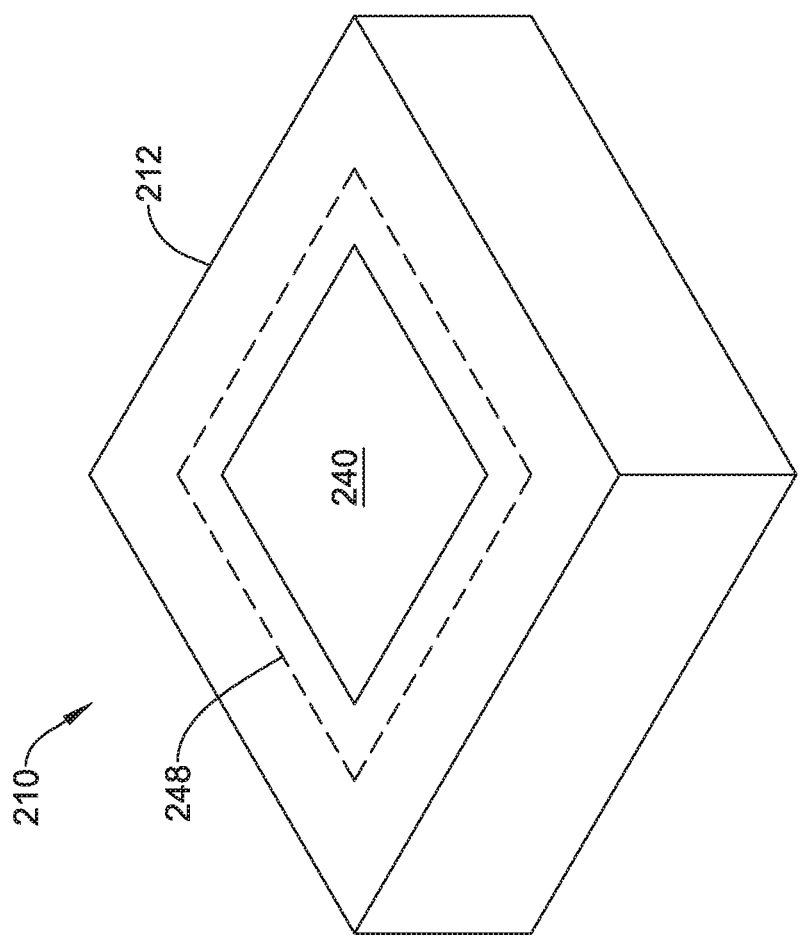
FIG. 6 is a schematic illustration of a package forming part of the system of FIG. 1, showing an inductive charging coil.

FIG. 6 provides a schematic illustration of a system 210 that includes a package 212. The system 210 may include some of the components described with respect to the system 10 (FIG. 1) or the system 110 (FIG. 4 and FIG. 5), although for simplicity these components are not illustrated in FIG. 6. In some cases, the system 210 may include an inductive charging system 240 that can be used to charge the medical device 18, 118 by placing the medical device 18, 118 near the inductive charging system 240. An inductive charging system 240 is essentially what is used in charging cell phones, for example, by placing the cell phone on an appropriate mat. In some cases, the inductive charging system 240 may also be used subsequent to sterilization to charge or recharge the power source 20 (FIG. 1 and FIG. 2) or the power source 120 (FIG. 4 and FIG. 5). These operations may be controlled or regulated, for example, by the controller 22 (FIG. 2). In some cases, the inductive charging system 240 may be protected by an encapsulating layer or film 248, but this is not required in all cases.

Figure 7:
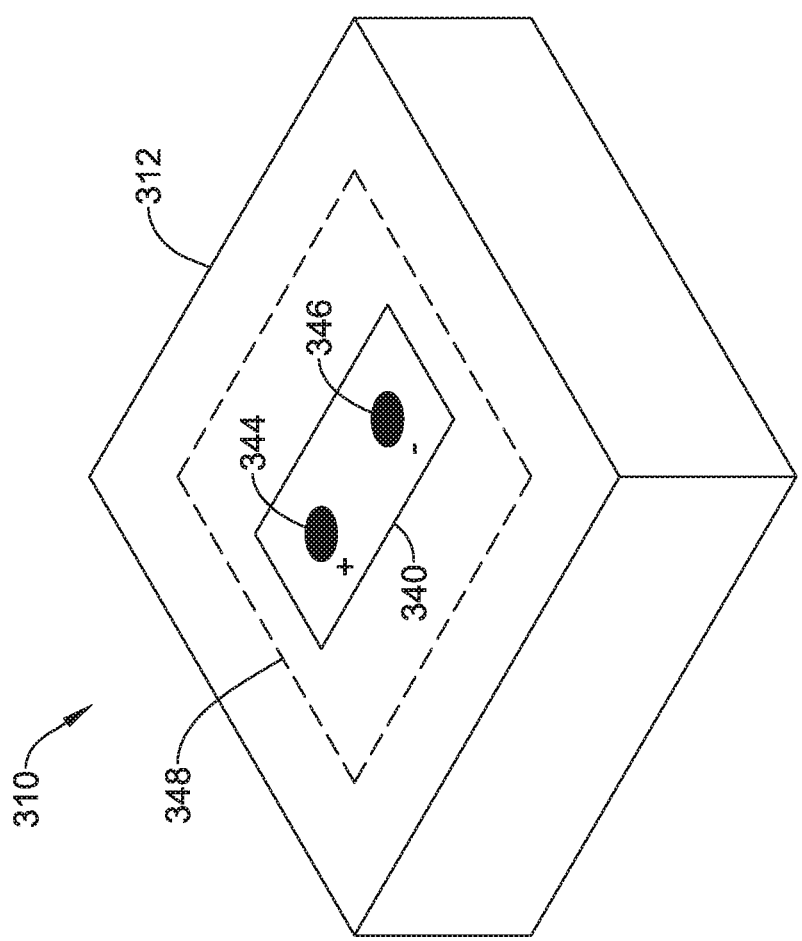
FIG. 7 is a schematic illustration of a package forming part of the system of FIG. 1, showing charging terminals.

FIG. 7 provides a schematic illustration of a system 310 that includes a package 312. The system 310 may include some of the components described with respect to the system 10 (FIG. 1) or the system 110 (FIG. 4 and FIG. 5), although for simplicity these components are not illustrated in FIG. 6. In some cases, the system 310 may include a charging system 340 that includes a (+) terminal 344 and a (−) terminal 346. In some instances, the charging system 340 is operably coupled to the power source (such as the power source 20, 120) disposed on or within the package 312, and thus can be used to charge the medical device 18, 118 by placing contacts on an exterior of the medical device 18, 118 in physical contact with the (+) terminal 344 and the (−) terminal 346. In some cases, the charging system 340 may also be used subsequent to sterilization to charge or recharge the power source 20 (FIG. 1 and FIG. 2) or the power source 120 (FIG. 4 and FIG. 5). These operations may be controlled or regulated, for example, by the controller 22 (FIG. 2). In some cases, the charging system 340 may be protected by an encapsulating layer or film 348, but this is not required in all cases.

Figure 8:
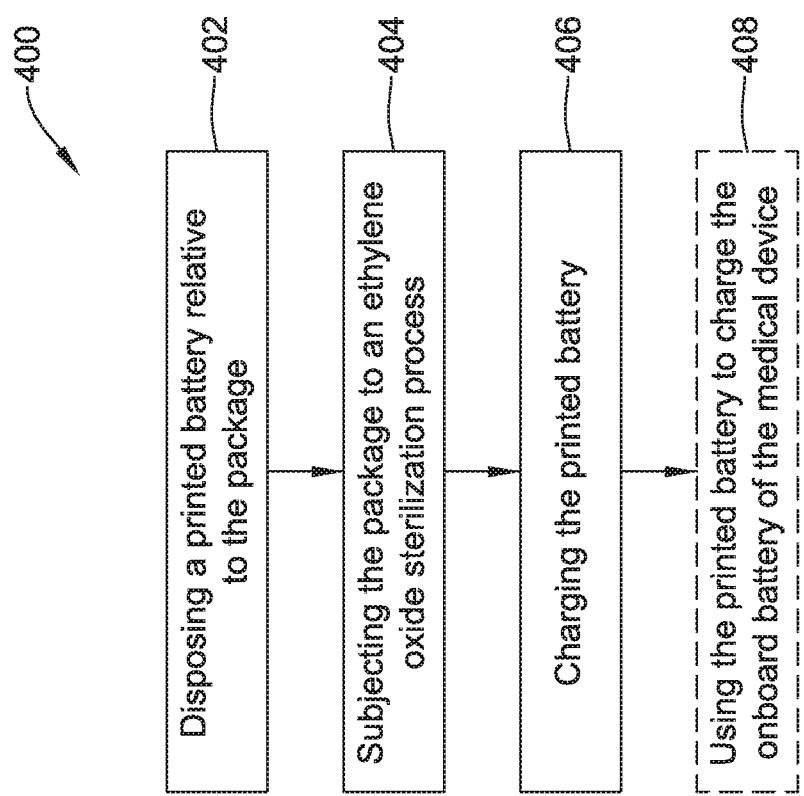
FIG. 8 is a flow diagram illustrating a method in accordance with an embodiment of the disclosure.

FIG. 8 is a flow diagram showing an illustrative method 400 of charging an onboard battery of a medical device using a package battery disposed within a package holding the medical device. A printed battery may be disposed relative to the package, as generally shown at block 402. In some cases, the printed battery may be configured to be safe during an ethylene oxide sterilization process. For example, the printed battery may be printed in a discharged state, or the printed battery may be at least partially encapsulated. The package may be subjected to an ethylene oxide sterilization process, as generally shown at block 404. As shown at block 406, the printed battery may subsequently be charged so that the printed battery can be used to charge the onboard battery of the medical device. In some cases, disposing a printed battery relative to the package includes printing a printed battery on a surface of the package, but this is not required in all cases. In some instances, as shown for example at block 408, the printed battery may be used to charge the onboard battery of the medical device.

Figure 9:
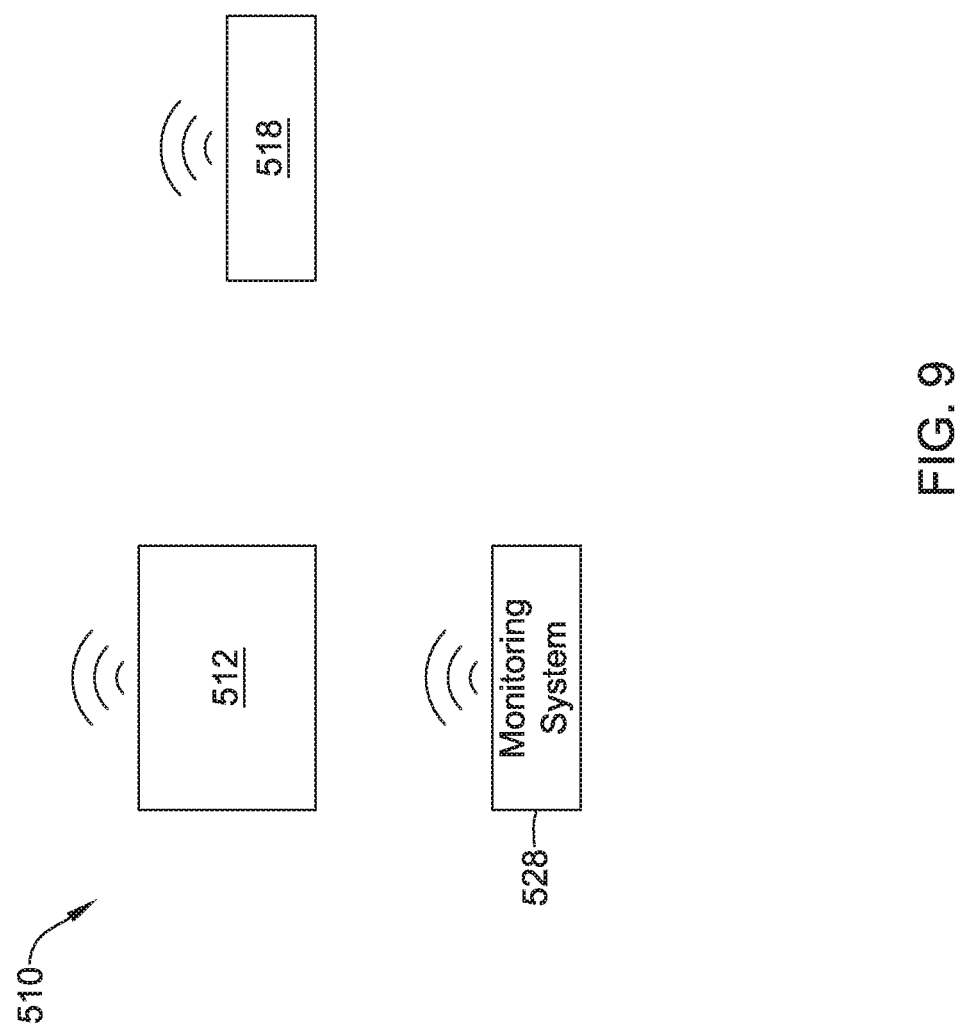
FIG. 9 is a schematic illustration of a system in which a medical device is in communication with a monitoring system via the packaging in which the medical device may be disposed.

In the systems discussed thus far, including the system 10 (FIG. 1), the system 110 (FIG. 4 and FIG. 5), the system 210 (FIG. 6) and the system 310 (FIG. 7), the emphasis has been on using a power source within the package 12, 112, 212, 312 to initially charge or to recharge a rechargeable battery 26 (FIG. 3) that is onboard the medical device 18, 118 prior to use of the medical device 18, 118. FIG. 9 shows a system 510 that includes a package 512 and a medical device 518. While not illustrated, the package 512 may be configured to charge or recharge a battery on-board the medical device 518 in much the same way as discussed with respect to the package 12, 112, 212, 312. However, in some cases the package 512 has additional capabilities. In some instances, the package 512 may be configured to communicate with the medical device 518, both while the medical device 518 remains within the package 512 but in some cases also even after the medical device 518 has been removed from the package 512. In some cases, the package 512, and thus the medical device 518, may be configured to communicate with a monitoring system 528. The monitoring system 528 may, for example, represent a computer within a medical facility.

In some cases, communication between the package 512 and the medical device 518 may provide the system 510 with a variety of useful functionality. For example, in some cases, the package 512 may include additional processing power that may supplement that available on board the medical device 518. The package 512 may include sensors that can be used to calibrate a sensor on board the medical device 518, for example. The package 512 may include dosage information that can be used to adjust a dosage of a medicine provided by the medical device 518. In some cases, the package 512 may be configured to monitor a charge of an on board battery of the medical device 518 so that the battery can be kept charged so that the medical device 518 may be ready for use at a moments notice.

Figure 10:
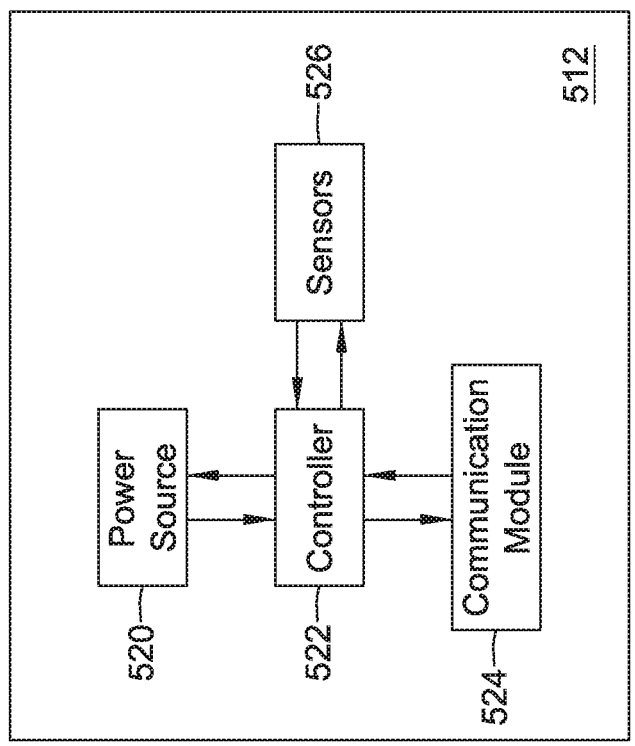
FIG. 10 is a schematic illustration of the packaging forming part of the system of FIG. 9.

FIG. 10 is a schematic illustration of the package 512, showing some of the features of the package 512. It will be appreciated that in some ways the package 512 is similar to the package 12, in that the package 512 includes a power source 520 and a controller 522. In some cases, the package 512 may include one or more sensors 526. In some cases, the sensors 526 may be useful in monitoring ambient conditions around the package 512, and thus around the medical device 518. Examples of suitable sensors include but are not limited to temperature sensors and pressure sensors. In some cases, for example, if the sensors 526 include an ambient pressure sensor, the sensors 526 can then provide the medical device 518 with a reference pressure sensor.

In some cases, the controller 522 may be operably coupled with a communication module 524 that enables communication between the package 512 and other devices such as, but not limited to, the medical device 518 and/or the monitoring system 528. In some cases, the communication module 524 may be configured to communicate wirelessly using any desired communication protocol such as, but not limited to, Wi-Fi or Bluetooth. In some cases, the controller 522 may use the communication module 524 to send and receive communication to and from the medical device 518. In some cases, the controller 522 may use the communication module 524 to send and receive communication to and from the medical device 518.

Figure 11:
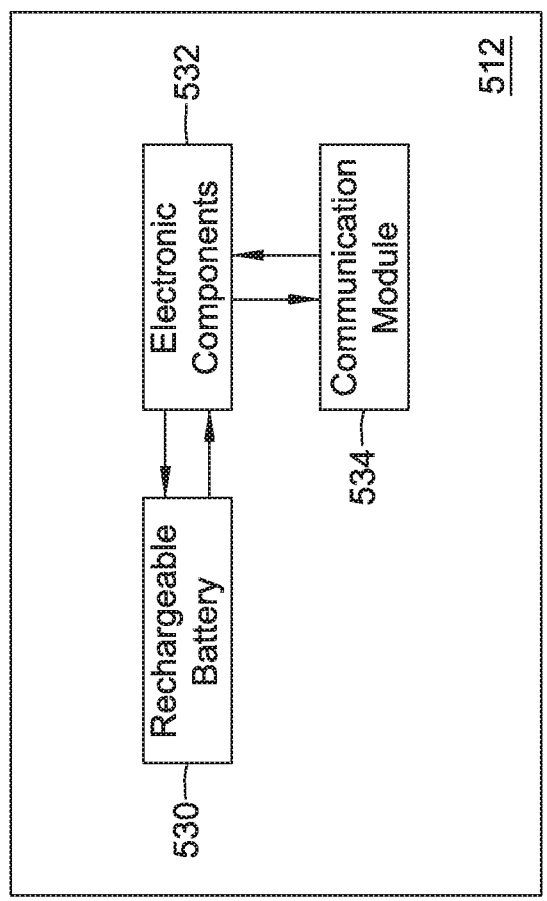
FIG. 11 is a schematic illustration of the medical device forming part of the system of FIG. 9.

FIG. 11 is a schematic illustration of the medical device 518, showing some of the features of the medical device 518. It will be appreciated that the medical device 518 may be similar to the medical device 18 (FIG. 3) in that the medical device 518 includes a rechargeable battery 530 and electronic components 532 that are powered by the rechargeable battery 530. In some cases, the medical device 518 includes a communication module 534 that enables the medical device 518 to communicate with the communication module 524 (FIG. 10) of the package 12.

It will be appreciated that a variety of different materials may be used in forming the packaging described herein. In some embodiments, for example, the packaging materials may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A system for charging an onboard battery of a medical device prior to use of the medical device, the system comprising:
   a package configured to accommodate a medical device within an interior of the package;
   a medical device disposed within the interior of the package, the medical device including an onboard rechargeable battery disposed within the medical device; and
   a power source disposed within the interior of the package and capable of charging the onboard rechargeable battery of the medical device prior to use of the medical device; and
   a controller disposed within the interior of the package and configured to use power stored within the power source to charge the onboard rechargeable battery disposed within the medical device prior to use of the medical device.

2. The system of claim 1, wherein the power source comprises a rechargeable battery.

3. The system of claim 2, wherein the rechargeable battery is uncharged during the sterilization process and is configured to subsequently be charged after the sterilization process.

4. The system of claim 2, wherein the rechargeable battery is at least partially encapsulated during the sterilization process.

5. The system of claim 2, wherein the rechargeable battery comprises a printed battery that is separately printed and subsequently disposed within the interior of the package.

6. The system of claim 2, wherein the rechargeable battery comprises a printed battery that is printed onto a surface of the interior.

7. The system of claim 1, further comprising an inductive charger operably coupled to the power source for inductively charging the onboard rechargeable battery of the medical device prior to use thereof.

8. The system of claim 1, further comprising a pair of electrical contacts operably coupled to the power source for directly charging the onboard rechargeable battery of the medical device prior to use thereof.

9. The system of claim 1, wherein when the controller is unable to recharge the onboard rechargeable battery of the medical device, or when the controller is unable to determine a power level of the onboard rechargeable battery, the controller denotes the system as defective.

10. A system for charging an onboard battery of a medical device prior to use of the medical device, the system comprising:
    a package configured to accommodate a medical device within an interior of the package;
    a medical device disposed within the interior of the package, the medical device including an onboard rechargeable battery disposed within the medical device; and
    a power source disposed within the interior of the package and capable of charging the onboard rechargeable battery of the medical device prior to use of the medical device;
    a display disposed relative to the package; and a controller disposed within the interior of the package and configured to monitor a remaining power level within the onboard rechargeable battery, the controller configured to display on the display the remaining power level within the onboard rechargeable battery.

11. The system of claim 10, wherein the controller is further configured to use power stored within the power source to charge the onboard rechargeable battery disposed within the medical device prior to use of the medical device.

12. The system of claim 10, wherein the power source comprises a rechargeable battery.

13. The system of claim 12, wherein the rechargeable battery is uncharged during the sterilization process and is configured to subsequently be charged after the sterilization process.

14. The system of claim 12, wherein the rechargeable battery is at least partially encapsulated during the sterilization process.

15. The system of claim 12, wherein the rechargeable battery comprises a printed battery.

16. A system for charging an onboard battery of a medical device prior to use of the medical device, the system comprising:
- a package configured to accommodate a medical device within an interior of the package;
- a medical device disposed within the interior of the package, the medical device including an onboard rechargeable battery disposed within the medical device; and
- a power source disposed within the interior of the package and capable of charging the onboard rechargeable battery of the medical device prior to use of the medical device;
- a display disposed relative to the package; and
- a controller disposed within the interior of the package and having a GPS capability, the controller configured to use power stored within the power source to charge the onboard rechargeable battery disposed within the medical device prior to use of the medical device when the controller determines that the package is at a location where use of the medical device may be imminent.

17. The system of claim 16, wherein the power source comprises a rechargeable battery.

18. The system of claim 16, wherein the rechargeable battery is uncharged during the sterilization process and is configured to subsequently be charged after the sterilization process.

19. The system of claim 16, wherein the rechargeable battery is at least partially encapsulated during the sterilization process.

20. The system of claim 16, wherein the rechargeable battery comprises a printed battery.

* * * * *